United States Patent
Ishiguro et al.

(10) Patent No.: US 12,251,271 B2
(45) Date of Patent: Mar. 18, 2025

(54) ULTRASOUND DIAGNOSTIC SYSTEM, ULTRASOUND DIAGNOSTIC APPARATUS, AND DIAGNOSIS ASSISTING SERVER

(71) Applicant: FUJIFILM Healthcare Corporation, Kashiwa (JP)

(72) Inventors: Suguru Ishiguro, Chiba (JP); Koji Waki, Chiba (JP); Akira Kusakabe, Chiba (JP); Eiji Kasahara, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 45 days.

(21) Appl. No.: 17/718,872

(22) Filed: Apr. 12, 2022

(65) Prior Publication Data

US 2022/0330925 A1 Oct. 20, 2022

(30) Foreign Application Priority Data

Apr. 19, 2021 (JP) ................. 2021-070479

(51) Int. Cl.
*A61B 8/08* (2006.01)
*A61B 8/00* (2006.01)
*G16H 50/20* (2018.01)

(52) U.S. Cl.
CPC ............. *A61B 8/565* (2013.01); *A61B 8/463* (2013.01); *A61B 8/5223* (2013.01); *G16H 50/20* (2018.01)

(58) Field of Classification Search
CPC ....... A61B 8/565; A61B 8/463; A61B 8/5223; A61B 8/5246; A61B 8/5292; A61B 8/465; A61B 8/44; A61B 8/06; A61B 8/4444; A61B 8/461; A61B 8/48; G16H 50/20; G16H 15/00; G16H 30/20; G16H 30/40; G16H 40/67

See application file for complete search history.

(56) References Cited

U.S. PATENT DOCUMENTS

| | | | |
|---|---|---|---|
| 2011/0257505 A1* | 10/2011 | Suri | G16H 50/30 600/443 |
| 2014/0094701 A1* | 4/2014 | Kwartowitz | A61B 8/5223 600/438 |
| 2019/0148011 A1 | 5/2019 | Rao et al. | |

(Continued)

FOREIGN PATENT DOCUMENTS

| | | | |
|---|---|---|---|
| CN | 102499716 A | * | 6/2012 |
| CN | 10883153 A | | 11/2018 |
| JP | 2004-8535 A | | 1/2004 |

(Continued)

OTHER PUBLICATIONS

Japanese official action dated Dec. 12, 2023 (and English translation thereof) in connection with Japanese Patent Application No. 2021-070479.

*Primary Examiner* — Boniface N Nganga
(74) *Attorney, Agent, or Firm* — Paul Teng

(57) ABSTRACT

A display frame data array is transferred from an ultrasound diagnostic apparatus to a diagnosis assisting server. The display frame data array is analyzed in the diagnosis assisting server, and a diagnosis assisting data array is generated. The diagnosis assisting data array is transferred from the diagnosis assisting server to the ultrasound diagnostic apparatus. A display processing unit combines the display frame data array and the diagnosis assisting data array while synchronizing the data arrays.

17 Claims, 9 Drawing Sheets

(56) References Cited

U.S. PATENT DOCUMENTS

2019/0388064 A1* 12/2019 Kezurer et al. ........... G06T 7/62

FOREIGN PATENT DOCUMENTS

| JP | 2004-110280 A | | 4/2004 |
|---|---|---|---|
| JP | 2006-187484 A | | 7/2006 |
| JP | 2009017991 A | * | 1/2009 |
| JP | 2016-85715 A | | 5/2016 |

* cited by examiner

ULTRASOUND DIAGNOSTIC SYSTEM, ULTRASOUND DIAGNOSTIC APPARATUS, AND DIAGNOSIS ASSISTING SERVER

CROSS REFERENCE TO RELATED APPLICATION

This application claims priority to Japanese Patent Application No. 2021-070479 filed on Apr. 19, 2021, which is incorporated herein by reference in its entirety including the specification, claims, drawings, and abstract.

TECHNICAL FIELD

The present disclosure relates to an ultrasound diagnostic system, an ultrasound diagnostic apparatus, and a diagnosis assisting server, and in particular to a technique for enabling cooperation of an ultrasound diagnostic apparatus and a diagnosis assisting server.

BACKGROUND

Ultrasound diagnostic apparatuses are becoming more and more sophisticated. However, because processing capabilities of the ultrasound diagnostic apparatus are finite, there may be cases where functions desired by developers or examiners (users) cannot be equipped on the ultrasound diagnostic apparatus. For example, such a phenomenon may occur when a machine learning-type CAD (Computer Aided Diagnosis) function is to be equipped. A configuration may be considered in which a still image acquired by the ultrasound diagnostic apparatus is transferred to an external apparatus (for example, a server), the server processes the still image, and the ultrasound diagnostic apparatus receives a result of the processing. However, with such a simple transfer of the image, ultrasound examination which is currently being performed cannot be assisted in real time.

Document 1 (JP 2016-85715 A) describes an ultrasound diagnostic system including a database and a plurality of ultrasound diagnostic apparatuses. The plurality of ultrasound diagnostic apparatuses share images and communicate with each other via chats. Document 1 does not describe image analysis or provision of a feedback of a result of the image analysis.

Document 2 (JP 2004-8535 A) describes an ultrasound diagnostic system including an ultrasound diagnostic apparatus and an external information processing apparatus. In the external information processing apparatus, measurement is executed for image data which are transferred from the ultrasound diagnostic apparatus, and a result of the measurement is transferred to the ultrasound diagnostic apparatus. Document 2 does not describe external processing in real time at the external information processing apparatus or real-time display of the external processing result at the ultrasound diagnostic apparatus.

While there is a limit in the degree of sophistication for the ultrasound diagnostic apparatus itself, it is desired to cause a separate apparatus to operate in parallel with the ultrasound diagnostic apparatus, to thereby provide in a timely manner analysis results of data to the examiner during a real-time operation, and assist probe operation and interpretation.

An advantage of the present disclosure lies in assisting the examiner during a real-time operation. Alternatively, another advantage of the present disclosure lies in assisting the probe operation and interpretation of the ultrasound image while not causing a heavy load for the ultrasound diagnostic apparatus.

SUMMARY

According to one aspect of the present disclosure, there is provided an ultrasound diagnostic system comprising: an ultrasound diagnostic apparatus; and a diagnosis assisting server connected to the ultrasound diagnostic apparatus via a network, wherein the ultrasound diagnostic apparatus comprises: a first transfer unit which transfers to the diagnosis assisting server a plurality of sets of frame data which are generated by transmission of ultrasound and reception of a reflected wave and which are in a time sequential order; and a display processing unit which displays the plurality of sets of frame data and a plurality of sets of diagnosis assisting data which are transferred from the diagnosis assisting server and which are in a time sequential order as a real-time video image, while synchronizing the plurality of sets of frame data and the plurality of sets of diagnosis assisting data, and the diagnosis assisting server comprises: a generator which generates the plurality of sets of diagnosis assisting data for assisting an examiner by analyzing the plurality of sets of frame data which are sent from the ultrasound diagnostic apparatus; and a second transfer unit which transfers the plurality of sets of diagnosis assisting data to the ultrasound diagnostic apparatus.

According to another aspect of the present disclosure, there is provided an ultrasound diagnostic apparatus connected to a diagnosis assisting server via a network, wherein the diagnosis assisting server generates a plurality of sets of diagnosis assisting data which are for assisting an examiner and which are in a time sequential order, by analyzing a plurality of sets of frame data which are sent from the ultrasound diagnostic apparatus and which are in a time sequential order, and transfers the plurality of sets of diagnosis assisting data to the ultrasound diagnostic apparatus, and the ultrasound diagnostic apparatus comprises: a transfer unit that transfers the plurality of sets of frame data to the diagnosis assisting server; and a display processing unit that displays the plurality of sets of frame data and the plurality of sets of diagnosis assisting data transferred from the diagnosis assisting server, while synchronizing the plurality of sets of frame data and the plurality of sets of diagnosis assisting data.

According to another aspect of the present disclosure, there is provided a diagnosis assisting server connected to an ultrasound diagnostic apparatus via a network, wherein the ultrasound diagnostic apparatus transfers to the diagnosis assisting server a plurality of sets of frame data which are generated by transmission of an ultrasound and reception of a reflected wave and which are in a time sequential order, and displays the plurality of sets of frame data and a plurality of sets of diagnosis assisting data which are transferred from the diagnosis assisting server and which are in a time sequential order, while synchronizing the plurality of sets of frame data and the plurality of sets of diagnosis assisting data, and the diagnosis assisting server comprises: a generator unit that generates the plurality of sets of diagnosis assisting data for assisting an examiner by analyzing the plurality of sets of frame data which are sent from the ultrasound diagnostic apparatus; and a transfer unit that transfers the plurality of sets of diagnosis assisting data to the ultrasound diagnostic apparatus.

BRIEF DESCRIPTION OF DRAWINGS

Embodiment(s) of the present disclosure will be described based on the following figures, wherein.

DESCRIPTION OF EMBODIMENTS

Figure 1:
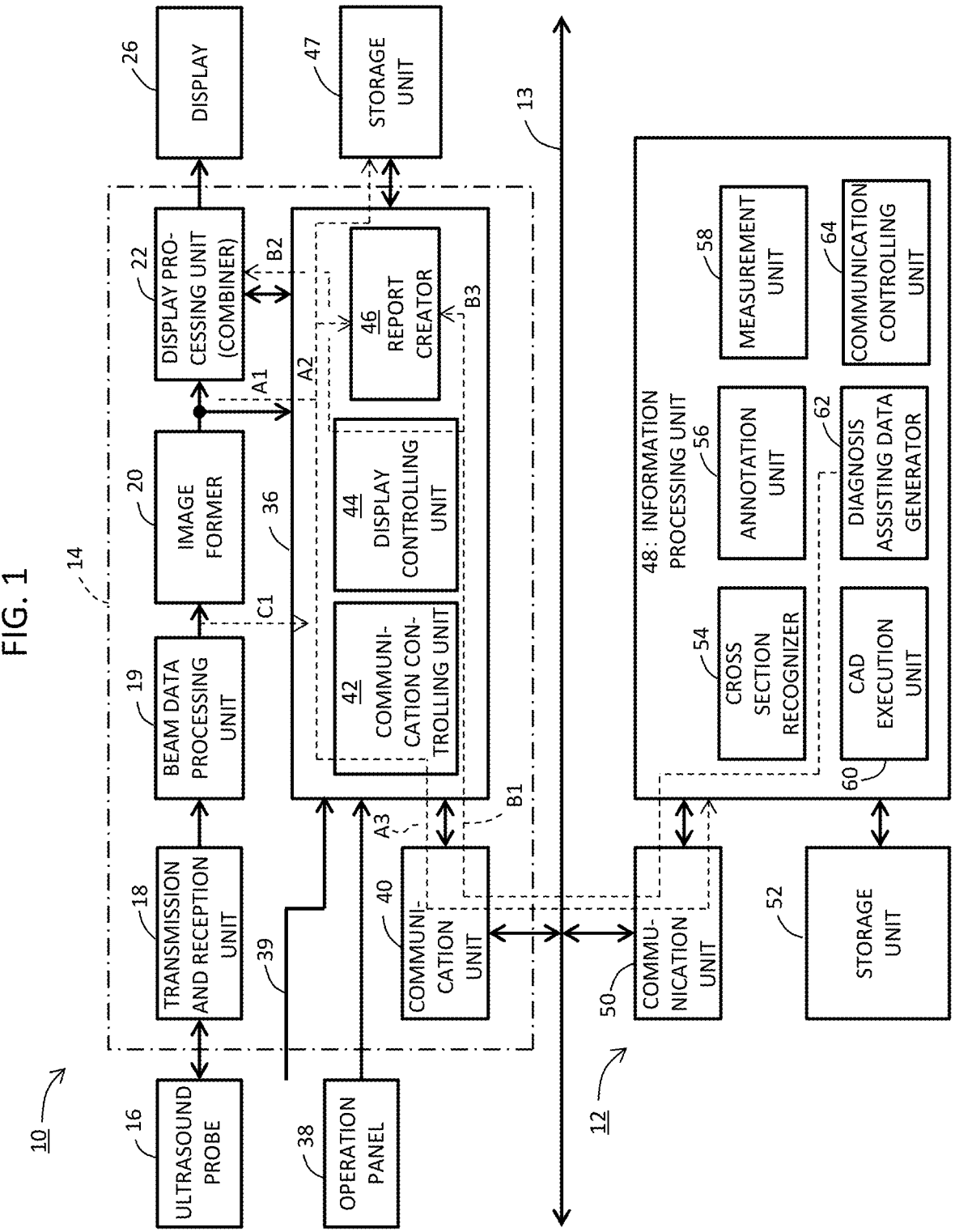
FIG. 1 is a block diagram showing an ultrasound diagnostic apparatus according to an embodiment of the present disclosure.

An embodiment of the present disclosure will now be described with reference to the drawings.

(1) Overview of Embodiment

An ultrasound diagnostic system according to an embodiment of the present disclosure comprises an ultrasound diagnostic apparatus, and a diagnosis assisting server connected to the ultrasound diagnostic apparatus via a network. The ultrasound diagnostic apparatus comprises a first transfer means (first transfer unit), and a display processing means (display processing unit). The first transfer means transfers to the diagnosis assisting server a plurality of sets of frame data which are generated by transmission of ultrasound and reception of a reflected wave and which are in a time sequential order. The display processing means displays the plurality of sets of frame data and a plurality of sets of diagnosis assisting data which are transferred from the diagnosis assisting server and which are in a time sequential order, as a real-time video image, while synchronizing the plurality of sets of frame data and the plurality of sets of diagnosis assisting data. The diagnosis assisting server comprises a generator means (generator) and a second transfer means (second transfer unit). The generator means generates a plurality of sets of diagnosis assisting data for assisting an examiner by analyzing the plurality of sets of frame data which are sent from the ultrasound diagnostic apparatus. The second transfer means transfers the plurality of sets of diagnosis assisting data to the ultrasound diagnostic apparatus.

According to the configuration described above, the ultrasound diagnostic apparatus and the diagnosis assisting server operate in parallel to each other and in real time. In the ultrasound diagnostic apparatus, the plurality of sets of diagnosis assisting data are displayed in a synchronized manner along with the plurality of sets of frame data. The probe can be operated and a lesion site may be observed while referring to the plurality of sets of diagnosis assisting data. With this configuration, the load imposed on the examiner can be reduced, or the ultrasound examination can be performed accurately.

In the above-described configuration, the synchronization means aligning or matching two sets of data in time. The real-time video image means a video image generated simultaneously with the transmission of the ultrasound and the reception of the reflected wave. The real-time video image momently reflects the most-recent echo information acquired from a tissue which is currently being observed. An operation for causing such a state is a real-time operation. The plurality of sets of frame data and the plurality of sets of diagnosis assisting data may be displayed on the same display, or may be displayed in separate displays. For the transfer, a technique such as streaming may be utilized. Alternatively, the diagnosis assisting server may be connected to a plurality of ultrasound diagnostic apparatuses, and a plurality of analyses for the plurality of ultrasound diagnostic apparatuses may be executed in parallel to each other.

In an embodiment of the present disclosure, the display processing means generates a plurality of sets of combined frame data by combining the plurality of sets of frame data and the plurality of sets of diagnosis assisting data while synchronizing the plurality of sets of frame data and the plurality of sets of diagnosis assisting data. The plurality of sets of combined frame data are displayed as the real-time video image. A part of each of the sets of diagnosis assisting data may be set as a combination target. According to this configuration, the plurality of sets of frame data and the plurality of sets of diagnosis assisting data are displayed on the same display.

In an embodiment of the present disclosure, each of the sets of frame data includes first synchronization information. Each of the sets of diagnosis assisting data includes second synchronization information. A combiner means combines the plurality of sets of frame data and the plurality of sets of diagnosis assisting data while synchronizing the plurality of sets of frame data and the plurality of sets of diagnosis assisting data, based on a plurality of sets of the first synchronization information included in the plurality of sets of frame data and a plurality of sets of the second synchronization information included in the plurality of sets of diagnosis assisting data. As the synchronization information, there may be exemplified a timestamp which identifies an acquisition timing or a processing timing of each individual set of reception data.

In an embodiment of the present disclosure, the generator means includes an analyzer means (analyzer) which analyzes the plurality of sets of frame data. A plurality of sets of diagnosis assisting data including a result of analysis by the analyzer means are generated. The analyzer means may be formed from, for example, a machine learning-type analyzer.

In an embodiment of the present disclosure, the analyzer means includes a means which applies a process for identifying a cross-section type on the plurality of sets of frame data. The real-time video image includes cross-section type information. The cross-section type is generally identified by a tissue and a cross section. A measurement to be performed or the like may be identified according to the identified cross-section type.

In an embodiment of the present disclosure, the analyzer means includes a means which performs measurement on the plurality of sets of frame data. The real-time video image includes measurement value information. In an embodiment of the present disclosure, the measurement value information includes a measurement value graph which changes dynamically. According to this configuration, all or a part of a frame data array may be set as a target of measurement, and a dynamically changing measurement value can be acquired. Alternatively, measurement may be performed on a still image at the diagnosis assisting server.

In an embodiment of the present disclosure, the analyzer means includes a means which applies computer diagnosis assistance including identification of a lesion site candidate on the plurality of sets of frame data. The real-time video image includes computer diagnosis assisting information. According to this configuration, the examiner who is observing the ultrasound image can be assisted in identification of the lesion site candidate or in evaluation diagnosis of the lesion site candidate.

In an embodiment of the present disclosure, the ultrasound diagnostic apparatus comprises a means (report creator) which creates an examination report based on all or a part of the plurality of sets of diagnosis assisting data. Alternatively, the creation of the examination report may be completely semi-automated or completely automated.

In an embodiment of the present disclosure, the first transfer means transfers to the diagnosis assisting server associated information necessary for analysis of the plurality of sets of frame data. As the associated information, there may be exemplified an electrocardiograph signal, coordinate information, weeks-of-pregnancy information, and the like.

An ultrasound diagnostic apparatus according to an embodiment of the present disclosure is an ultrasound diagnostic apparatus connected to a diagnosis assisting server via a network. The diagnosis assisting server generates a plurality of sets of diagnosis assisting data which are for assisting an examiner and which are in a time sequential order, by analyzing a plurality of sets of frame data which are sent from the ultrasound diagnostic apparatus and which are in a time sequential order, and transfers to the ultrasound diagnostic apparatus the plurality of sets of diagnosis assisting data. The ultrasound diagnostic apparatus comprises a transfer means and a display processing means. The transfer means transfers the plurality of sets of frame data to the diagnosis assisting server. The display processing means displays the plurality of sets of frame data and the plurality of sets of diagnosis assisting data transferred from the diagnosis assisting server, while synchronizing the plurality of sets of frame data and the plurality of sets of diagnosis assisting data.

A diagnosis assisting server according to an embodiment of the present disclosure is a diagnosis assisting server connected to an ultrasound diagnostic apparatus via a network. The ultrasound diagnostic apparatus transfers to the diagnosis assisting server a plurality of sets of frame data which are generated by transmission of ultrasound and reception of a reflected wave and which are in a time sequential order, and displays the plurality of sets of frame data and the plurality of sets of diagnosis assisting data which are transferred from the diagnosis assisting server and which are in a time sequential order, while synchronizing the plurality of sets of frame data and the plurality of sets of diagnosis assisting data. The diagnosis assisting server comprises a generator means and a transfer means. The generator means generates the plurality of sets of diagnosis assisting data for assisting an examiner by analyzing the plurality of sets of frame data which are sent from the ultrasound diagnostic apparatus. The transfer means transfers the plurality of sets of diagnosis assisting data to the ultrasound diagnostic apparatus.

(2) Details of Embodiment

FIG. 1 shows an ultrasound diagnostic system according to an embodiment of the present disclosure. The ultrasound diagnostic system is a medical system which is equipped, for example, in a medical organization, and which generates and displays an ultrasound image in real time based on information acquired by transmission of ultrasound to a living body and reception of a reflected wave from inside of the living body.

The ultrasound diagnostic system is formed from an ultrasound diagnostic apparatus 10 and a diagnosis assisting server 12 which are connected to each other via a network 13. The network 13 is provided, for example, in the medical organization, and is a wired or wireless LAN (Local Area Network). Alternatively, the network 13 may be formed from a dedicated line. The diagnosis assisting server 12 has a function which is beyond the function provided in the ultrasound diagnostic apparatus 10. Alternatively, a plurality of ultrasound diagnostic apparatuses may be connected to the diagnosis assisting server 12, and the same service or different services may be provided to the plurality of ultrasound diagnostic apparatuses.

FIG. 1 shows a configuration in which the ultrasound diagnostic apparatus 10 and the diagnosis assisting server 12 operate in a cooperating manner. In the following, the structure of the ultrasound diagnostic apparatus 10 will be described assuming selection of a B mode (tomographic image display mode), and the structure of the diagnosis assisting server 12 will then be described.

The ultrasound diagnostic apparatus 10 comprises a body 14. An ultrasound probe 16 is detachably connected to the body 14. As the ultrasound probe 16, there are known a probe which is used in contact with a body surface of an examination target, a probe which is used by being inserted into a body cavity of the examination target, and the like. The ultrasound probe 16 comprises, for example, a transducer array including a plurality of transducers which are one-dimensionally arranged. An ultrasound beam is formed by the transducer array, and is electronically scanned. Alternatively, a transducer array including a plurality of transducers which are two-dimensionally arranged may be provided in the ultrasound probe 16.

A transmission and reception unit 18 supplies a plurality of transmission signals to the transducer array in parallel to each other, during transmission. During reception, the transmission and reception unit 18 applies a predetermined processing (such as amplification, A/D conversion, delay, summing, or the like) to a plurality of reception signals which are output from the transducer array in parallel to each other. With this process, beam data are generated. With repetition of electronic scanning of the ultrasound beam, a reception frame data array is output from the transmission and reception unit 18.

The reception frame data array is formed from a plurality of sets of reception frame data which are arranged on a time axis. Each individual set of reception frame data is formed from a plurality of sets of beam data arranged in the direction of the electronic scan. Each individual set of beam data is formed from a plurality of sets of echo data arranged in the depth direction. A beam data processing unit 19 is provided downstream of the transmission and reception unit 18. Processing such as wave detection, logarithmic transformation, or the like is applied to each set of beam data in the beam data processing unit 19.

An image former 20 generates a display frame data array based on the reception frame data array. The image former has a DSC (Digital Scan Converter). The DSC is formed from a processor having a coordinate conversion function, a pixel interpolation function, or the like. In the present embodiment, each individual set of display frame data corresponds to a tomographic image. Each set of reception frame data and each set of display frame data respectively correspond to image data.

A display processing unit 22 is a display processing means or a combiner means, and has an image combining function, a color processing function, or the like. The display processing unit 22 temporarily stores the display frame data array which is output from the image former 20, and combines a diagnosis assisting data array which is transferred from the diagnosis assisting server to the display frame data array, to thereby generate a combined display frame data array.

In this process, the display processing unit 22 combines data which match in time. That is, the display processing unit 22 functions as a combiner which performs synchronous combination. In order to realize the synchronous combination, each individual set of display frame data includes a timestamp serving as time information, and, similarly, each individual set of diagnosis assisting data includes a timestamp serving as time information. The display processing unit 22 also combines a graphic data array to the display frame data array. Alternatively, another configuration may be considered in which the display frame data array and the diagnosis assisting data array are synchronously displayed without being synchronously combined.

In a real-time operation, the display frame data array is displayed as a real-time video image, namely as a real-time moving image, on a screen of a display 26. A display image of a particular time phase is displayed as a still image in a frozen state in which the transmission and the reception are suspended. The display 26 is formed from a liquid crystal display, an organic EL device, or the like.

For example, the timestamp may be embedded with respect to each individual set of display frame data in the image former 20, or the timestamp may be embedded with respect to each individual set of display frame data in an information processing unit 36 to be described below, or the like. In the diagnosis assisting server 12, when a certain set of display frame data is processed, the timestamp embedded therein is extracted, and the extracted timestamp is embedded in the diagnosis assisting data including a result of analysis of the display frame data. In this manner, the timestamp is ported from the analysis target to the analysis result, so that the synchronous combining or the synchronous display at the ultrasound diagnostic apparatus 10 can be reliably performed.

The information processing unit 36 executes control of operations of various elements of the ultrasound diagnostic apparatus 10. In addition, the information processing unit 36 executes control necessary for causing the diagnosis assisting server 12 to cooperate. The information processing unit 36 is formed from a processor which executes a program. The processor is more specifically a CPU (Central Processing Unit). In FIG. 1, a plurality of functions realized by the processor are represented by a plurality of blocks. That is, the information processing unit 36 includes a communication controlling unit 42, a display controlling unit 44, and a report creator 46.

A communication unit 40 is connected to the information processing unit 36. The communication controlling unit 42 functions as a first transfer means or a first transfer unit. The communication controlling unit 42 controls data transfer via the communication unit 40, in particular, the transfer of the display frame data array from the ultrasound diagnostic apparatus 10 to the diagnosis assisting server 12.

The display controlling unit 44 controls display processing by the display processing unit 22. The report creator 46 is a module which semi-automatically or automatically creates an examination report. The report creator 46 functions as a report creator means. The examination report may include the diagnosis assisting data generated by the diagnosis assisting server 12. Alternatively, the report creator 46 may be provided in the diagnosis assisting server 12.

A storage unit 47 connected to the information processing unit 36 is formed from a semiconductor memory or the like, and stores various data. The examination report may be stored in the storage unit 47. An operation panel 38 connected to the information processing unit 36 includes a plurality of switches, a plurality of knobs, a trackball, or the like. The operation panel 38 functions as an inputting unit. An electrocardiograph signal 39 is input to the information processing unit 36 as associated information. Alternatively, other associated information may be input.

Next, the diagnosis assisting server 12 will be described. The diagnosis assisting server 12 is formed from a computer, and has an information processing unit 48, a communication unit 50, and a storage unit 52. The information processing unit 48 executes a plurality of functions. These functions are represented by a plurality of blocks in FIG. 1.

Specifically, in the illustrated example structure, the information processing unit 48 has a cross section recognizer 54, an annotation unit 56, a measurement unit 58, a CAD execution unit 60, a diagnosis assisting data generator 62, and a communication controlling unit 64. Of these elements, the cross section recognizer 54, the annotation unit 56, the measurement unit 58, the CAD execution unit 60, and the diagnosis assisting data generator 62 correspond to a generator means or a generator. In addition, of these elements, the cross section recognizer 54, the annotation unit 56, the measurement unit 58, and the CAD execution unit 60 correspond to an analyzer means or an analyzer. The information processing unit 48 is formed from a processor which executes a program. The processor is, for example, a CPU.

The cross section recognizer 54 applies cross section recognition to each set of display frame data. In other words, the cross section recognizer 54 applies a process for identifying a cross-section type on a plurality of sets of display frame data. For example, the cross section recognizer 54 is formed from a machine learning-type image estimator. The cross-section type is identified by the cross section recognizer 54. For example, as the cross-section type, a four-chamber view of a heart, a two-chamber view of the heart, or the like is identified. The cross section recognizer 54 also has a function for estimating certainty in regard to the recognition (probability that the recognition is correct). A result of the recognition and information on the certainty are sent from the cross section recognizer 54 to the diagnosis assisting data generator 62.

The annotation unit 56 identifies each site in the cross section as necessary, based on the result of the cross section recognition, and attaches a label (site name) to the identified site. For example, a name such as "aortic valve" is attached. The attached information is sent to the diagnosis assisting data generator 62.

The measurement unit 58 executes measurement for each set of display frame data in a real-time operation state. The measurement unit 58 also performs measurement on a particular set of display frame data or other data in a frozen state in which the transmission and reception are suspended. Examples of measurements performed on the tomographic image include a distance measurement, an area measurement, a volume measurement, or the like. Alternatively, a location and a type of the measurement may be selected based on the recognized cross section. In the present embodiment, in the real-time operation state, a measurement value is calculated for each set of display frame data, and a measurement value array is sent from the measurement unit 58 to the diagnosis assisting data generator 62.

Alternatively, measurement may be performed on an ultrasound image other than the tomographic image in the measurement unit 58. For example, as will be described later, measurement (such as automatic tracing and time measurement) may be performed on a Doppler waveform. When such a processing is executed, the Doppler waveform may be transferred from the ultrasound diagnostic apparatus 10 to the diagnosis assisting server 12 with a display frame rate, or with another rate.

The CAD execution unit 60 executes CAD. In the present embodiment, the CAD execution unit 60 has a function for identifying, for each set of display frame data, a lesion site candidate included in the display frame data (that is, the tomographic image), and a function for generating information for assisting the diagnosis for the lesion site candidate (possible disease name, operation guide, or the like). Alternatively, the CAD execution unit 60 may be formed from a machine learning-type image analyzer. Information generated by the CAD execution unit 60 is sent to the diagnosis assisting data generator 62.

The diagnosis assisting data generator 62 generates diagnosis assisting data (feedback data) for each set of display frame data. The diagnosis assisting data may include cross-section recognition information, annotation information, measurement result information, CAD execution result information, or the like.

The diagnosis assisting data generator 62 has a function for extracting the timestamp included in the display frame data which is the analysis target, and a function for embedding the extracted timestamp with respect to the diagnosis assisting data which is the analysis result. Alternatively, such a porting process may be executed by another module such as the communication controlling unit 64.

In the diagnosis assisting data generator 62, a diagnosis assisting data array corresponding to the display frame data array is generated. Alternatively, different frame rates may be employed for the display frame data array and the diagnosis assisting data array. For example, a frame rate of the latter may be set to be ½ the frame rate of the former. In this case, a set of diagnosis assisting data which is the closest in time to each set of display frame data may be correlated to the display frame data in the display processing unit 22. Such a correlation is one form of the synchronous combination. An alternative configuration may be considered in which, in order to reduce a load of the diagnosis assisting server 12, a portion of the received display frame data array is set as the analysis target. A further alternative configuration may be considered in which a portion of the display frame data array generated by the ultrasound diagnostic apparatus 10 is transferred to the diagnosis assisting server.

The communication controlling unit 64 controls data transfer via the communication unit 50, in particular, the transfer of the diagnosis assisting data array from the diagnosis assisting server 12 to the ultrasound diagnostic apparatus 10. The communication controlling unit 64 corresponds to a second transfer means or a second transfer unit. The storage unit 52 is connected to the information processing unit 48. The storage unit 52 stores the display frame data array, various analysis results, the diagnosis assisting data array, or the like, as necessary.

The communication unit 40 and the communication unit 50 are connected to each other via the network 13. As described above, the network 13 is formed from the wired LAN or the wireless LAN. The network is installed in the medical organization. Alternatively, the network 13 may be the Internet.

In the ultrasound diagnostic apparatus 10, when a color flow mapping mode (CFM mode) and a pulse Doppler mode (PW mode) are simultaneously selected, beam scanning for B mode, beam scanning for color Doppler, and beam formation for Doppler observation are executed according to a predetermined transmission and reception sequence.

A first display frame data array is generated based on a first reception frame data array acquired by the beam scanning for B mode. A second display frame data array is generated based on a second reception frame data array acquired by the beam scanning for color Doppler. In the present embodiment, only the first display frame data array is transferred and analyzed, but alternatively, the second display frame data array may be additionally transferred and analyzed.

Through transmission and reception in a particular direction, Doppler information is extracted from a sample gate which is set on the particular direction, and a power spectrum is generated through frequency analysis of the Doppler information. The power spectrum generated at each time phase is mapped on the time axis, to generate a Doppler waveform. For example, the frequency analysis is executed at the beam data processing unit 19, and the Doppler waveform is generated at the image former 20.

For example, the Doppler waveform may be transferred to the diagnosis assisting server 12 at a timing of an image store operation in a frozen state, and the Doppler waveform may be analyzed in the diagnosis assisting server 12. Alternatively, the Doppler waveform may be transferred in units of display frames, and may be measured in real time. Alternatively, an image other than the above-described images may be transferred to the diagnosis assisting server 12.

According to the embodiment shown in FIG. 1, because the ultrasound image and the diagnosis assisting data are displayed as real-time video images, the examiner may operate the probe and perform image diagnosis while referring to the diagnosis assisting data. Because the image analysis is automatically performed in the background, the load for the examiner is not increased in the image analysis, and the load of the examiner can thus be significantly reduced in comparison to that in the conventional art. In other words, the examiner can concentrate on the probe operation and the image observation. According to the present embodiment, the ultrasound examination time can also be shortened, the load for the examination target may also be reduced.

Alternatively, the reception frame data array may be transferred from the ultrasound diagnostic apparatus 10 to the diagnosis assisting server 12. In this case, the DSC may be provided in the diagnosis assisting server 12. Alternatively, in the frozen state, the transfer of the display frame data array may be temporarily suspended. A configuration may be employed in which, in this state, only the data necessary for the diagnosis assisting server 12 are transferred.

Figure 2:
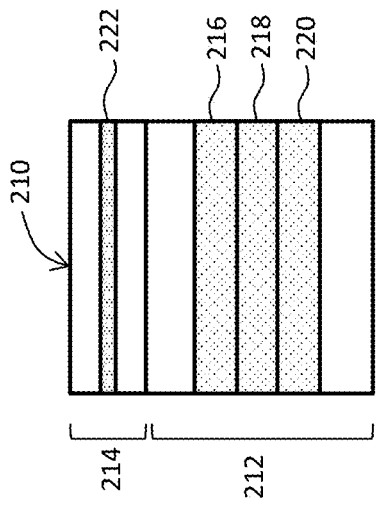
FIG. 2 is a diagram showing an example structure of display frame data.

FIG. 2 shows an example of the display frame data. A set of display frame data 200 is formed from a data substance 202 and a header 204. The header 204 is attribute information of the data substance 202, and includes a timestamp 206. In addition, the header 204 may include information such as a frame number, a mode, depth information, a transmission frequency, or the like.

Figure 3:
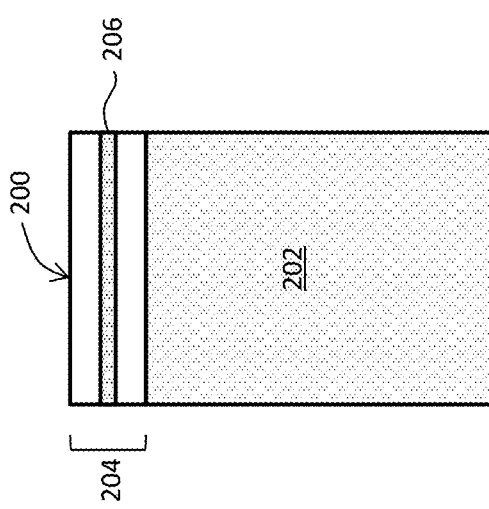
FIG. 3 is a diagram showing an example structure of diagnosis assisting data.

FIG. 3 shows an example of the diagnosis assisting data. A set of diagnosis assisting data 210 is formed from a data substance 212 and a header 214. The data substance 212 includes cross-section recognition result information 216, measurement result information 218, and CAD execution result information 220. The header 214 further includes a timestamp 222.

Figure 4:
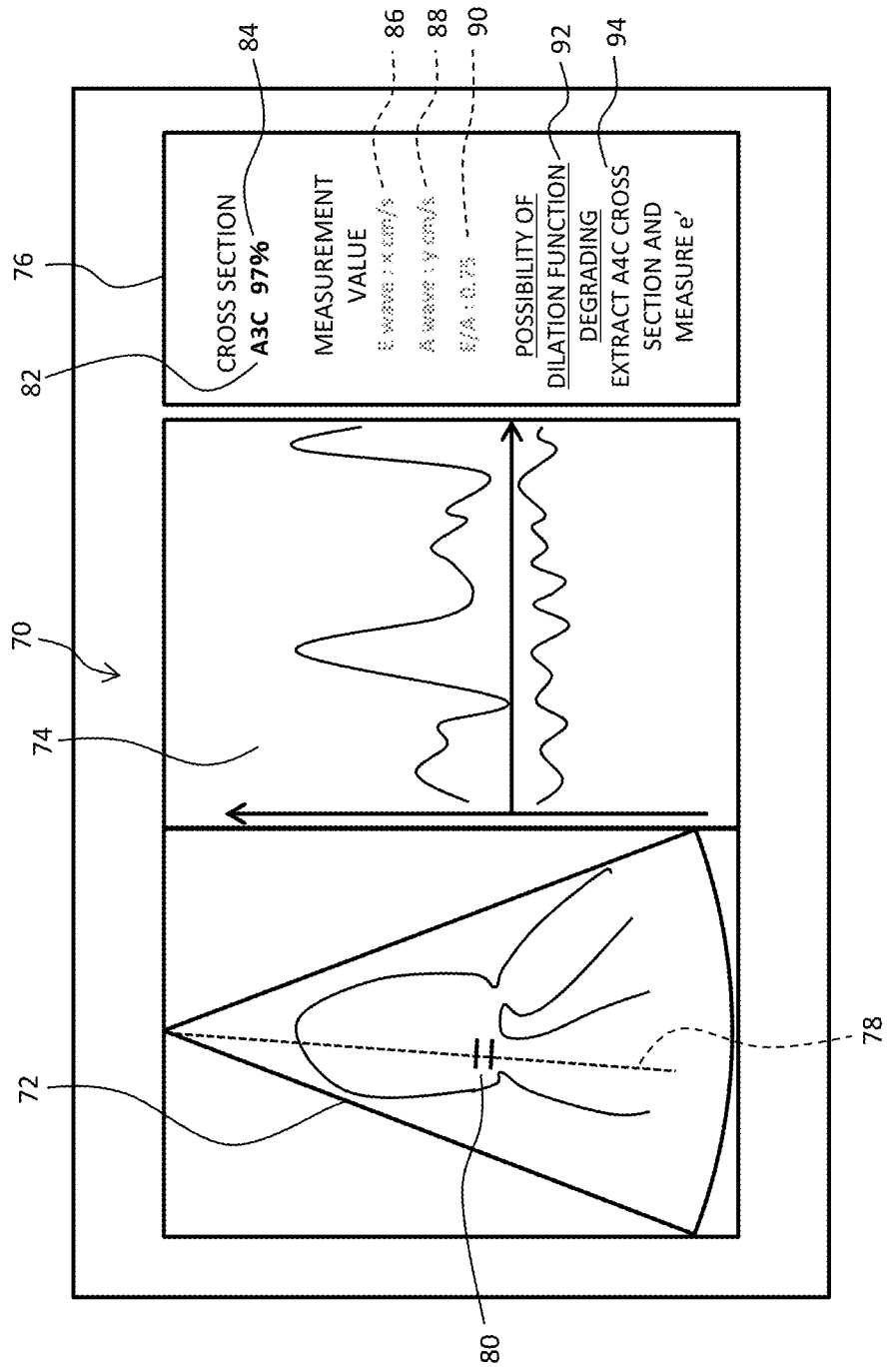
FIG. 4 is a diagram showing a first example display.

FIG. 4 shows a first display example. A display image 70 is a real-time video image displayed on the display of the ultrasound diagnostic apparatus. In the illustrated example, the display image 70 has a CFM image 72, a Doppler waveform 74, and a diagnosis assisting image 76. The CFM image 72 is a composite image generated by combining a color Doppler image (bloodstream image) on a B-mode tomographic image. A direction marker 78 is included in the CFM image 72, and a gate marker 80 which shows a sample gate position is displayed on the direction marker 78. In the Doppler waveform 74, the horizontal axis is a time axis, and the vertical axis is a velocity axis. Intensity or power of each velocity component is correlated with brightness.

In the illustrated example, the diagnosis assisting image 76 includes information 82 showing the cross-section type, a numerical value 84 showing the certainty of the cross-section type, and information 92 and 94 showing the CAD execution result. These information show the result of the image analysis executed for each frame, and may change dynamically. The information 92 is information for explaining a possible disease, and the information 94 is information for guiding an operation or diagnosis which should be executed next.

In the first display example shown in FIG. 4, at the point in time when the image store operation is executed in the frozen state, the Doppler waveform which is being displayed at the point in time is transferred from the ultrasound diagnostic apparatus to the diagnosis assisting server. With this process, three measurements are automatically executed on the transferred Doppler waveform at the diagnosis assisting server. As a result, three measurement values 86, 88, and 90 are displayed in the diagnosis assisting image 76.

Figure 5:
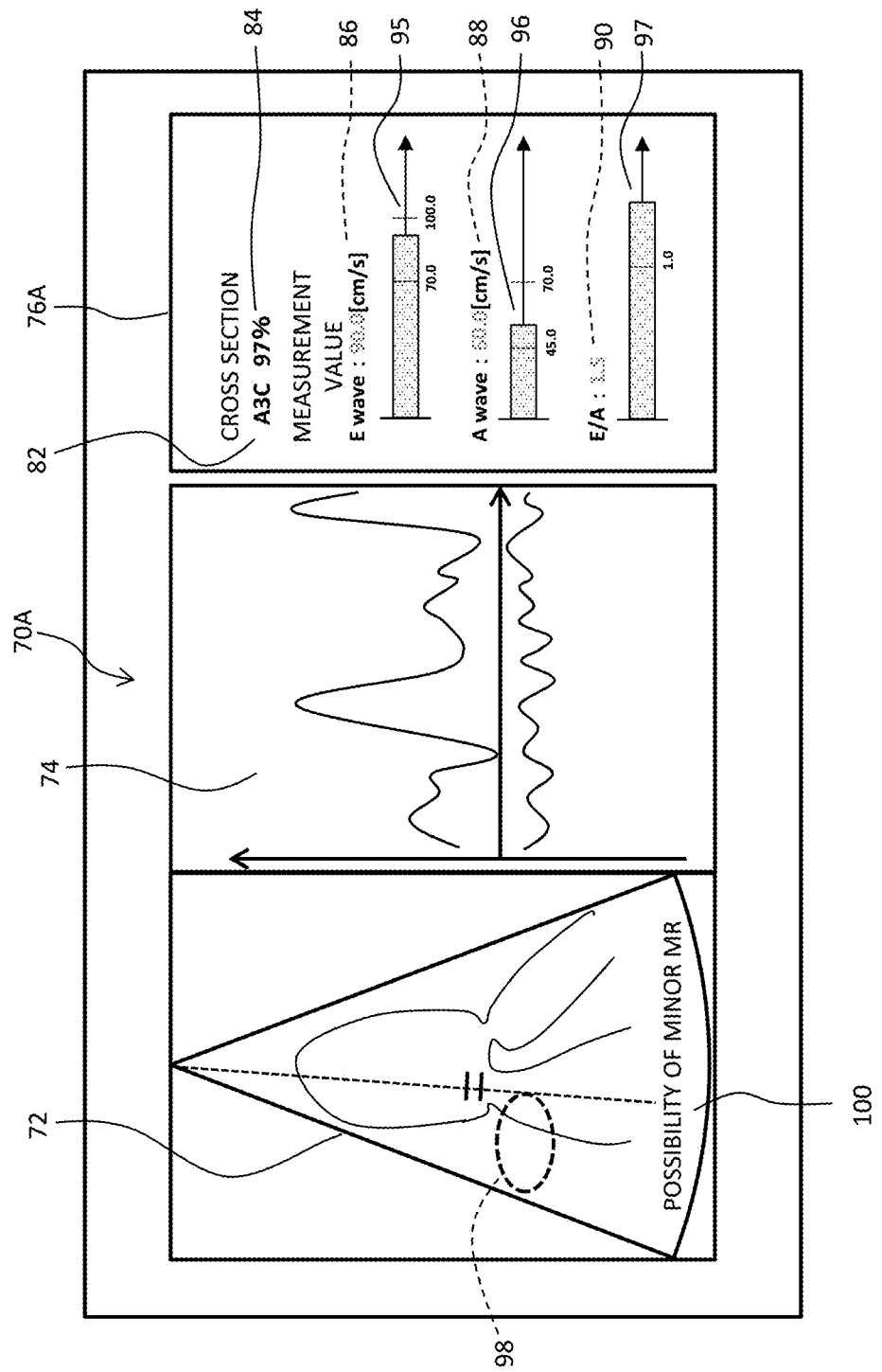
FIG. 5 is a diagram showing a second example display.

FIG. 5 shows a second display example. In FIG. 5, elements similar to those already described above are assigned the same reference numerals, and the description of these elements will not be repeated. This is similarly applicable to FIG. 6 and later figures.

In the second display example, a display image 70A includes the CFM image 72, the Doppler waveform 74, and a diagnosis assisting image 76A. The CFM image 72 includes a marker 98 and information 100. The marker 98 is a figure surrounding the lesion site candidate. A position of the lesion site candidate is identified by the CAD execution unit. The information 100 is information generated by the CAD execution unit, and is more specifically information showing the possible disease. The marker 98 and the information 100 are updated for each frame.

In the second display example, the diagnosis assisting image 76A includes three measurement value graphs 95, 96, and 97. That is, each of the measurement value graphs 95, 96, and 97 shows a measurement value which changes with a frame rate or with another rate. Each of the measurement value graphs 95, 96, and 97 has an axis showing the size of the measurement value, and two numerical values showing an upper limit and a lower limit of a normal range (or a standard range) are displayed on the axis. When the second display example is employed, for example, the Doppler waveform which is updated in units of frames is transferred from the ultrasound diagnostic apparatus to the diagnosis assisting server. In this case, all of the frame data may be transferred or only an updated portion may be transferred. When the examiner performs the image store operation in the frozen state, the three measurement values 86, 88, and 90 are displayed as numerical values.

Figure 6:
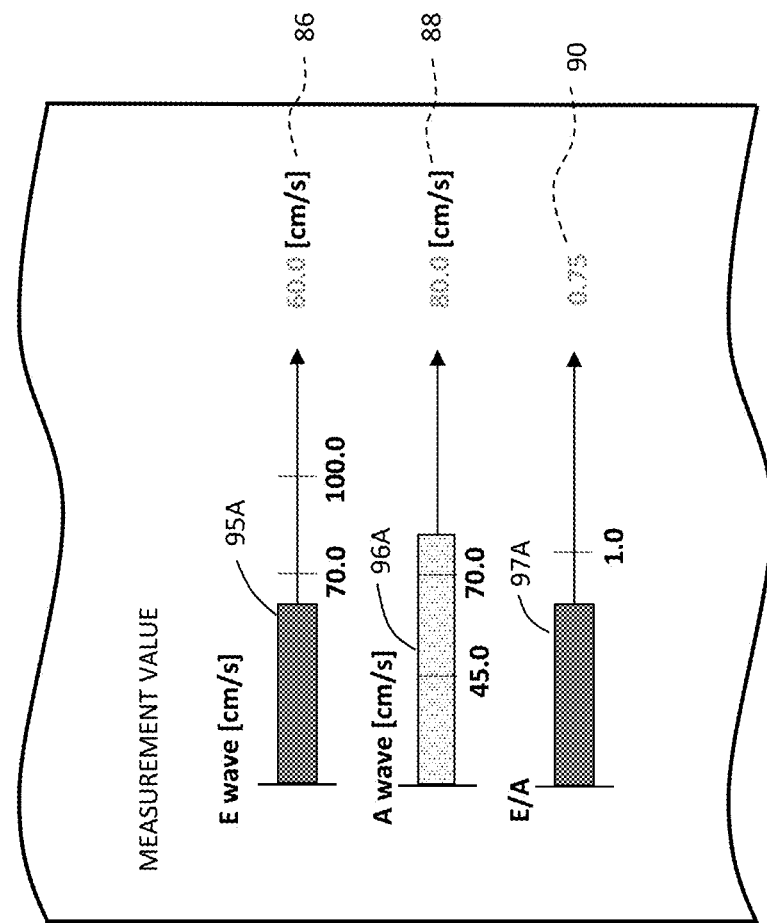
FIG. 6 is a diagram showing an alternative example of the second example display.

FIG. 6 shows an alternative configuration of the second display example. During display of each of measurement value graphs 95A, 96A, and 97A, when each measurement value is included in the normal range, each of the measurement value graphs 95A, 96A, and 97A is displayed with a first color (for example, green), and, when any of the measurement values falls outside of the normal range, the measurement value graph 95A, 96A, or 97A corresponding thereto is displayed with a second color (for example, orange). Alternatively, a representation method other than a bar graph may be employed.

Figure 7:
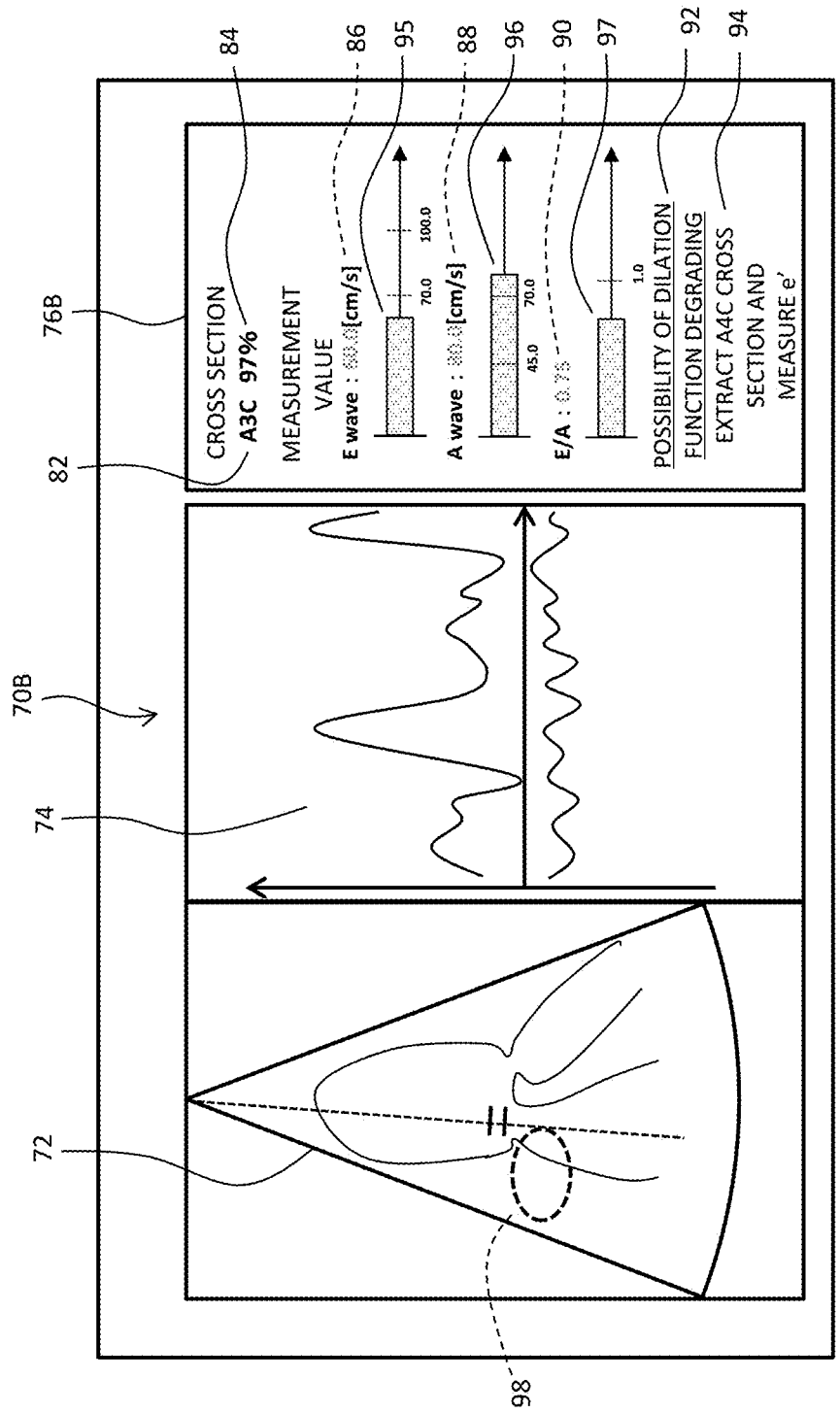
FIG. 7 is a diagram showing a third example display.

FIG. 7 shows a third display example. A display image 70B includes the CFM image 72, the Doppler waveform 74, and a diagnosis assisting image 76B. The CFM image 72 includes the marker 98 showing the lesion site candidate. The diagnosis assisting image 76B includes the information 82 showing the cross-section type, the information 84 showing the certainty, the three measurement value graphs 95, 96, and 97, and the information 92 and 94. The information 92 is information for explaining a possible disease, and the information 94 is information for guiding an operation which is recommended to be performed next.

Figure 8:
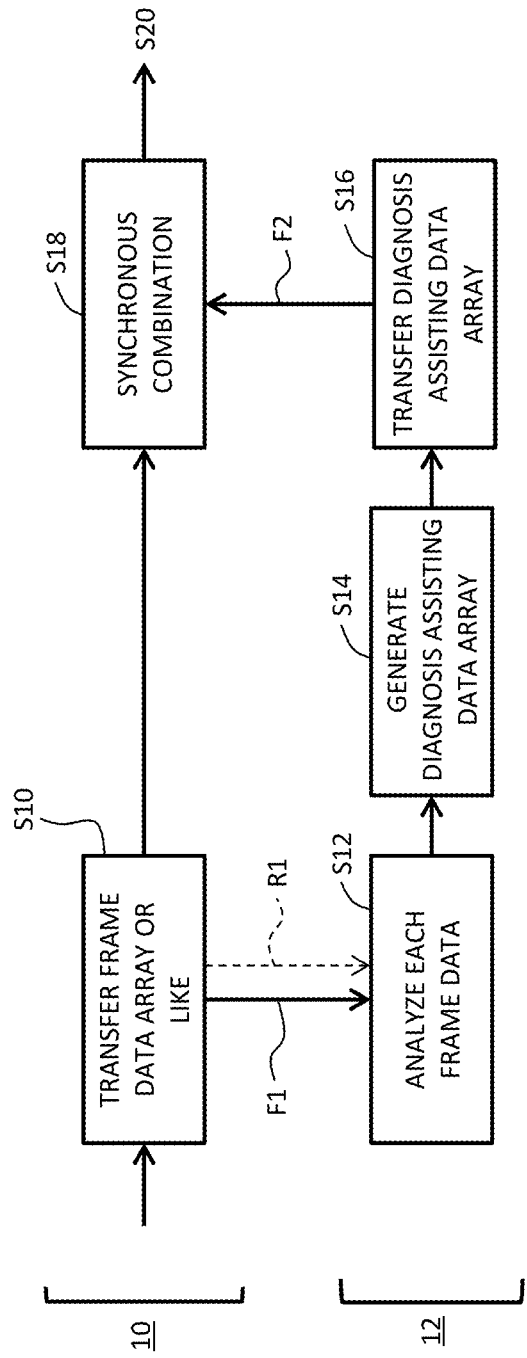
FIG. 8 is a process diagram showing an example operation of an ultrasound diagnostic apparatus.

FIG. 8 shows an example operation of the ultrasound diagnostic system according to the present embodiment. Specifically, FIG. 8 shows an example operation of the ultrasound diagnostic apparatus 10 and an example operation of the diagnosis assisting server 12. In S10, a plurality of sets of display frame data F1 are sequentially transferred from the ultrasound diagnostic apparatus 10 to the diagnosis assisting server 12. In S12, each set of display frame data is sequentially analyzed in the diagnosis assisting server 12. The analysis includes the cross section recognition, the measurement, the identification of the lesion site, or the like. In S14, a plurality of sets of diagnosis assisting data are sequentially generated in the diagnosis assisting server 12, and, in S16, the plurality of sets of diagnosis assisting data F2 are sequentially transferred from the diagnosis assisting server 12 to the ultrasound diagnostic apparatus 10. In S18, the plurality of sets of display frame data and the plurality of sets of diagnosis assisting data are sequentially synchronously combined in the ultrasound diagnostic apparatus 10, to thereby generate a plurality of sets of combined display frame data. For the synchronous combination, two sets of data are matched in time.

In the transfer of the plurality of sets of display frame data F1, or at a necessary timing, associated information R1 necessary for the image analysis in the diagnosis assisting server 12 may be transferred. Examples of the associated information R1 include, for example, an electrocardiograph signal, probe position information, weeks-of-pregnancy information, and the like.

Figure 9:
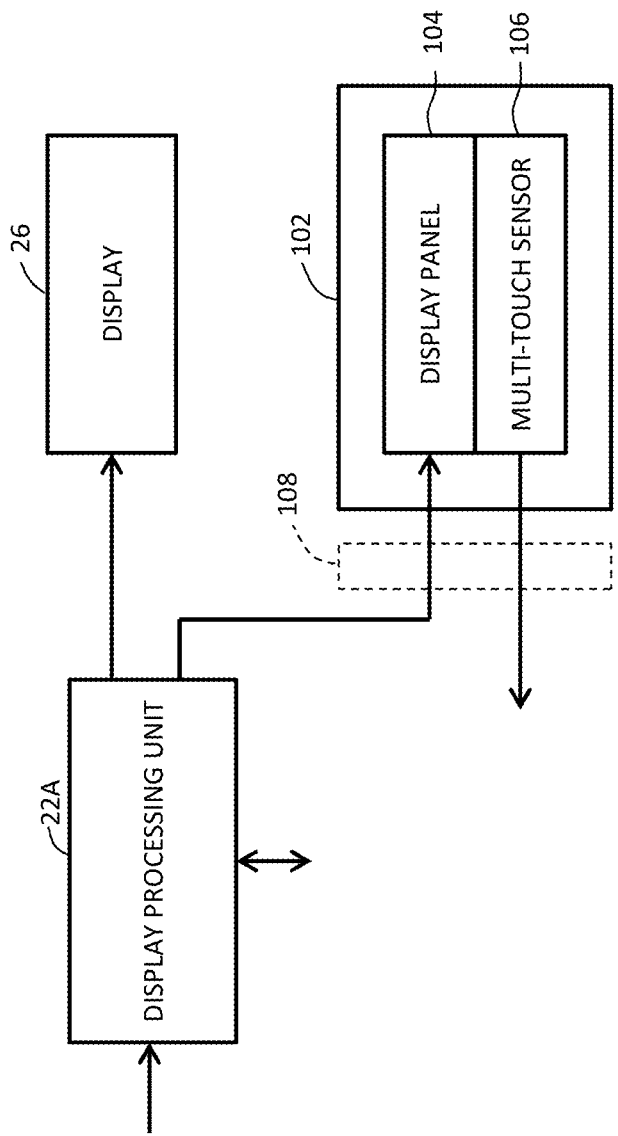
FIG. 9 is a diagram showing a structure of a part of an ultrasound diagnostic apparatus according to an alternative configuration.

FIG. 9 shows an alternative configuration of the ultrasound diagnostic apparatus. The ultrasound diagnostic apparatus comprises a transportable or fixedly-placed touch screen panel 102. The touch screen panel 102 is a stacked structure of a display panel 104 and a multi-touch sensor 106. First image information is sent from a display controlling unit 22A to the display 26, and second image information is sent from the display processing unit 22A to the touch screen panel 102. The first image information is, for example, information including one or a plurality of ultrasound images. The first image information may include all or a part of the diagnosis assisting data. The second image information includes the diagnosis assisting data.

The display controlling unit 22A executes a display process so that two sets of data in a synchronous relationship are simultaneously displayed on two displays. In this manner, the display processing unit 22A executes synchronous display. Alternatively, a part of the data may be synchronously combined in the display processing unit 22A. As shown by reference numeral 108, the touch screen panel 102 is connected to the ultrasound diagnostic apparatus via a wire or wirelessly.

Figure 10:
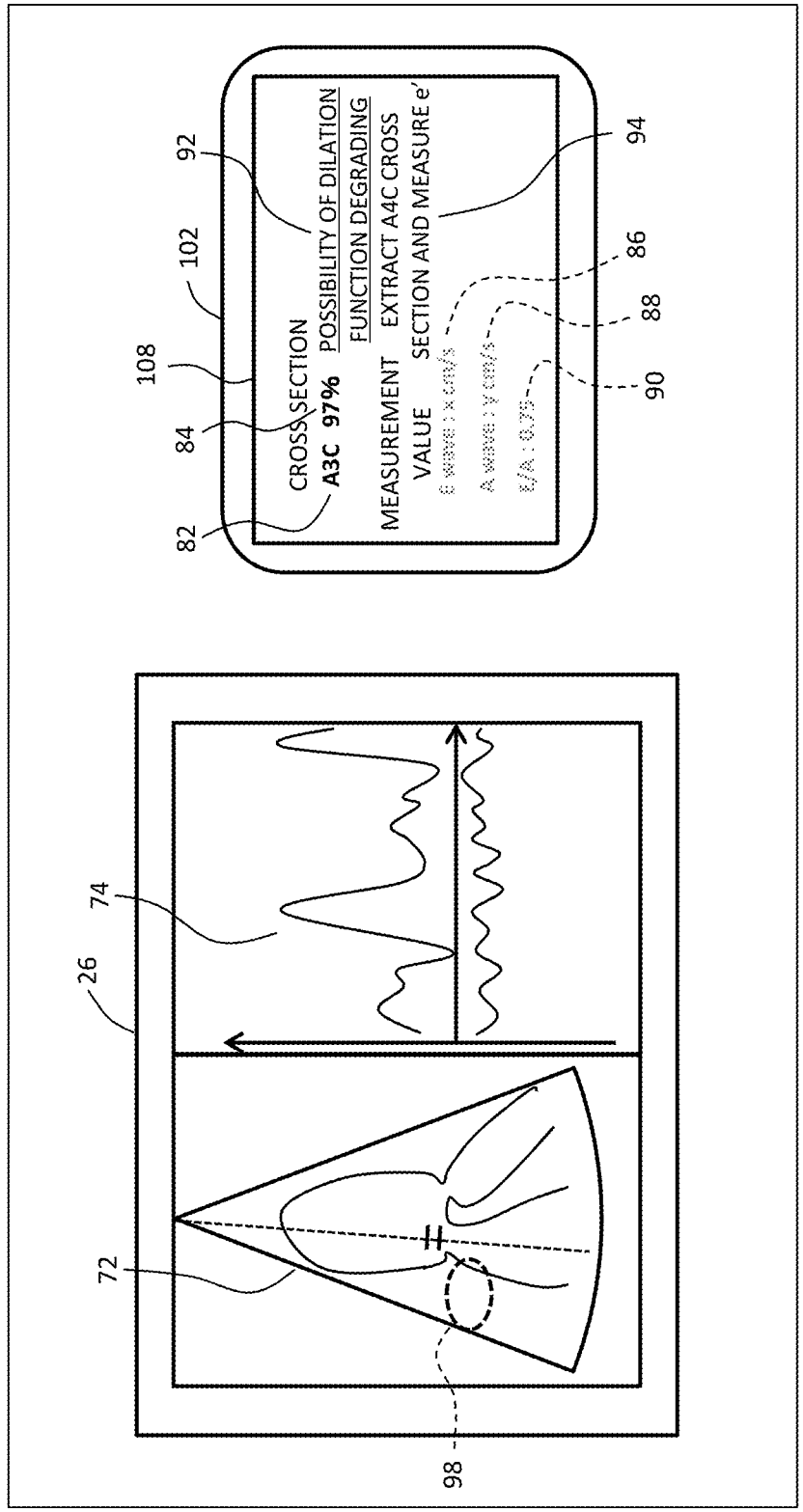
FIG. 10 is a diagram showing an example display of the ultrasound diagnostic apparatus according to the alternative configuration.

FIG. 10 shows an example display in the alternative configuration. The CFM image 72 and the Doppler waveform 74 are displayed on the display 26. A part of the diagnosis assisting data, more specifically, the marker 98 showing the lesion site candidate, is displayed on the CFM image 72. The diagnosis assisting image 108 including various information 82, 84, 92, and 94 generated by the image analysis is displayed on the touch screen panel 102. For example, when a store operation of the image is performed in the frozen state, three measurements are executed, and three measurement values 86, 88, and 90 showing the measurement results are displayed. In this alternative configuration also, because the probe operation and the observation of the ultrasound image can be executed while referring to the diagnosis assisting data, the examiner can be assisted.

The invention claimed is:

1. An ultrasound diagnostic system comprising:
a diagnosis assisting server; and
an ultrasound diagnostic apparatus connected to the diagnosis assisting server via a network, the ultrasound diagnostic apparatus comprising:
a first transfer unit which transfers to the diagnosis assisting server a plurality of sets of frame data, the plurality of sets of frame data having been generated by transmission of ultrasound and reception of a reflected wave and include, in a time sequential order, a plurality of sets of first synchronization information being embedded in the plurality of sets of frame data, respectively; and
a display processing unit which generates a plurality of sets of combined frame data by combining the plurality of sets of frame data and a plurality of sets of diagnosis assisting data, the plurality of sets of diagnosis assisting data having been transferred from the diagnosis assisting server, the display processing unit synchronizing the plurality of sets of frame data and the plurality of sets of diagnosis assisting data based on (i) the plurality of sets of first synchronization information included in the plurality of sets of frame data and (ii) a plurality of sets of second synchronization information included in the plurality of sets of diagnosis assisting data, and the display processing unit displaying the plurality of sets of combined frame data as a real-time video image,
wherein the diagnosis assisting server comprises:
a generator which generates the plurality of sets of diagnosis assisting data for assisting an examiner by analyzing the plurality of sets of frame data which are sent from the ultrasound diagnostic apparatus, the plurality of sets of second synchronization information being embedded in the plurality of sets of diagnosis assisting data, respectively, based on the plurality of sets of first synchronization information included in the plurality of sets of frame data; and
a second transfer unit which transfers the plurality of sets of diagnosis assisting data to the ultrasound diagnostic apparatus, and wherein
in the diagnosis assisting server, the plurality of sets of first synchronization information are extracted from the plurality of sets of frame data, the extracted plurality of sets of first synchronization information being embedded in the plurality of sets of diagnosis assisting data as the plurality of sets of second synchronization information.

2. The ultrasound diagnostic apparatus according to claim 1, wherein
the generator includes an analyzer which analyzes the plurality of sets of frame data, and
the plurality of sets of diagnosis assisting data including a result of analysis by the analyzer are generated.

3. The ultrasound diagnostic system according to claim 2, wherein
the analyzer applies a process for identifying a cross-section type on the plurality of sets of frame data, and
the real-time video image includes cross-section type information.

4. The ultrasound diagnostic system according to claim 2, wherein
the analyzer performs measurement on the plurality of sets of frame data, and
the real-time video image includes measurement value information.

5. The ultrasound diagnostic system according to claim 4, wherein
the measurement value information includes a measurement value graph which changes dynamically.

6. The ultrasound diagnostic system according to claim 2, wherein
the analyzer applies computer diagnosis assistance including identification of a lesion site candidate on the plurality of sets of frame data, and
the real-time video image includes computer diagnosis assisting information.

7. The ultrasound diagnostic system according to claim 2, wherein
the first transfer unit transfers to the diagnosis assisting server associated information necessary for analysis of the plurality of sets of frame data.

8. The ultrasound diagnostic system according to claim 1, wherein
the ultrasound diagnostic apparatus comprises a report creator which creates an examination report based on all or a part of the plurality of sets of diagnosis assisting data.

9. An ultrasound diagnostic apparatus connected to a diagnosis assisting server via a network, wherein the diagnosis assisting server generates a plurality of sets of diagnosis assisting data which are for assisting an examiner and which are in a time sequential order, by analyzing a plurality of sets of frame data which are sent from the ultrasound diagnostic apparatus and which are in a time sequential order, and transfers the plurality of sets of diagnosis assisting data to the ultrasound diagnostic apparatus, the ultrasound diagnostic apparatus comprising:
a transfer unit that transfers the plurality of sets of frame data to the diagnosis assisting server, a plurality of sets of first synchronization information being embedded in the plurality of sets of frame data, respectively; and
a display processing unit that generates a plurality of sets of combined frame data by combining the plurality of sets of frame data and a plurality of sets of diagnosis assisting data, the plurality of sets of diagnosis assisting data having been transferred from the diagnosis assisting server, the display processing unit synchronizing the plurality of sets of frame data and the plurality of sets of diagnosis assisting data based on (i) the plurality of sets of first synchronization information included in the plurality of sets of frame data and (ii) a plurality of sets of second synchronization information included in the plurality of sets of diagnosis assisting data, the display processing unit displaying the plurality of sets of combined frame data as a real-time video image, wherein in the diagnosis assisting server, the plurality of sets of first synchronization information are extracted from the plurality of sets of frame data, the extracted plurality of sets of first synchronization information being embedded in the plurality of sets of diagnosis assisting data as the plurality of sets of second synchronization information.

10. The ultrasound diagnostic apparatus according to claim 9, further comprising a report creator which creates an examination report based on all or a part of the plurality of sets of diagnosis assisting data.

11. The ultrasound diagnostic apparatus according to claim 9, wherein the transfer unit transfers to the diagnosis assisting server associated information necessary for analysis of the plurality of sets of frame data.

12. A diagnosis assisting server connected to an ultrasound diagnostic apparatus via a network, wherein the ultrasound diagnostic apparatus transfers to the diagnosis assisting server a plurality of sets of frame data, the plurality of sets of frame data having been generated by transmission of ultrasound and reception of a reflected wave and include, in a time sequential order, a plurality of sets of first synchronization information being embedded in the plurality of sets of frame data, respectively, the ultrasound diagnostic apparatus generating a plurality of sets of combined frame data by combining the plurality of sets of frame data and a plurality of sets of diagnosis assisting data, the plurality of sets of diagnosis assisting data having been transferred from the diagnosis assisting server, the ultrasound diagnostic apparatus synchronizing the plurality of sets of frame data and the plurality of sets of diagnosis assisting data based on (i) the plurality of sets of first synchronization information included in the plurality of sets of frame data and (ii) a plurality of sets of second synchronization information included in the plurality of sets of diagnosis assisting data, and the ultrasound diagnostic apparatus displaying the plurality of sets of frame data and a plurality of sets of diagnosis assisting data which are transferred from the diagnosis assisting server and which are in a time sequential order, while synchronizing the plurality of sets of frame data and the plurality of sets of diagnosis assisting data, the diagnosis assisting server comprising:

a generator that generates the plurality of sets of diagnosis assisting data for assisting an examiner by analyzing the plurality of sets of frame data which are sent from the ultrasound diagnostic apparatus; and a transfer unit that transfers the plurality of sets of diagnosis assisting data to the ultrasound diagnostic apparatus, the plurality of sets of second synchronization information being embedded in the plurality of sets of diagnosis assisting data, respectively, based on the plurality of sets of first synchronization information included in the plurality of sets of frame data, in the diagnosis assisting server, the plurality of sets of first synchronization information are extracted from the plurality of sets of frame data, the extracted plurality of sets of first synchronization information being embedded in the plurality of sets of diagnosis assisting data as the plurality of sets of second synchronization information.

13. The diagnosis assisting server according to claim 12, wherein the generator includes an analyzer which analyzes the plurality of sets of frame data, and the plurality of sets of diagnosis assisting data generated by the generator include a result of analysis by the analyzer.

14. The diagnosis assisting server according to claim 13, wherein the analyzer applies a process for identifying a cross-section type on the plurality of sets of frame data, and the real-time video image includes cross-section type information.

15. The diagnosis assisting server according to claim 13, wherein the analyzer performs measurement on the plurality of sets of frame data, and the real-time video image includes measurement value information.

16. The diagnosis assisting server according to claim 15, wherein the measurement value information includes a measurement value graph which changes dynamically.

17. The diagnosis assisting server according to claim 13, wherein the analyzer applies computer diagnosis assistance including identification of a lesion site candidate on the plurality of sets of frame data, and the real-time video image includes computer diagnosis assisting information.

* * * * *